United States Patent [19]

Koppert

[11] Patent Number: 5,089,020
[45] Date of Patent: * Feb. 18, 1992

[54] MONOSEPTAL, BI-VENTRICULAR ARTIFICIAL HEART

[75] Inventor: Erik Koppert, Salt Lake City, Utah
[73] Assignee: University of Utah Research Foundation, Salt Lake City, Utah
[*] Notice: The portion of the term of this patent subsequent to Jan. 18, 2007 has been disclaimed.
[21] Appl. No.: 383,668
[22] Filed: Jul. 24, 1989
[51] Int. Cl.⁵ ............................................. A61Z 1/10
[52] U.S. Cl. ..................................... 623/3; 600/16
[58] Field of Search ..................... 623/3; 600/16-18

[56] References Cited

U.S. PATENT DOCUMENTS

| | | | |
|---|---|---|---|
| 3,766,567 | 10/1973 | Kahn et al. | 623/3 |
| 3,916,449 | 11/1975 | Davis | 623/3 |
| 4,427,470 | 1/1984 | Kolff | 623/3 X |
| 4,573,997 | 3/1986 | Wisman et al. | 623/3 |
| 4,750,903 | 6/1988 | Cheng | 623/3 |
| 4,785,795 | 11/1988 | Singh | 600/18 |

*Primary Examiner*—Ronald Frinks
*Attorney, Agent, or Firm*—Thorpe, North & Western

[57] ABSTRACT

A total artificial heart, comprising a heart enclosure and an interior rigid septum attached at its periphery to the interior surface of the heart enclosure. This septum divides the heart into two separate pumping chambers corresponding to left and right ventricles. The septum has opposing nonplanar faces including a curved wave form with an "S" configuration to increase the surface area of the septum to be almost equal to the surface area of the interior surface of opposing chambers of the heart enclosure. This construction avoids overlapping of the attached pumping diaphragm with resultant stress and consequential failure. Also disclosed is a double lumen drive line which facilitates percutaneous entry of the required flow drive system.

11 Claims, 3 Drawing Sheets

MONOSEPTAL, BI-VENTRICULAR ARTIFICIAL HEART

BACKGROUND OF THE INVENTION

1. Field of Invention

The present invention relates to a total artificial heart which includes opposing pumping compartments, each having a pumping chamber and blood chamber confined within a heart enclosure. More particularly, the present invention relates to an improved single septum and coupled diaphragm configuration which separates the respective configuration compartments.

2. Prior Art

Increased effort over the last decade to generate an effective total artificial heart has resulted in numerous variations in housing, chamber, valve, and diaphragm design, placement relationship for the respective left and right ventricle, improved drive systems and numerous other technical enhancements intended to generate a reliable total artificial heart. Ultimately, however, success of the total artificial heart will rest primarily on its predictability and long-term survivability within the patient. Such long term use depends on the ability of the constantly oscillating diaphragms to perform their function of drawing blood within a blood chamber and expelling it to establish circulation to maintain life-sustaining circulation. In fact, many of the design features for various ventricles are specifically generated to enhance the survivability and reliability of the blood pumping diaphragm.

One of the more common heart designs involves the use of a pumping chamber which relies on a rigid wall or base and an attached flexible diaphragm and which is extended and retracted by reason of positive and, if necessary, negative pneumatic pressure applied through a connecting drive line to one side of the diaphragm. An opposing side of this diaphragm forms a partial, interior wall of a blood chamber, corresponding to the pumping ventricle of the natural heart. The use of a rigid wall in the pumping chamber forces the more flexible diaphragm to extend away from the wall in response to pneumatic pressure.

One limiting factor of efficiency for this total artificial heart system is a requirement that the diaphragm be protected against localized stress which weakens the diaphragm and eventually results in failure. Early heart designs utilized a body having a spherical configuration wherein the pumping diaphragm assumed a retracted position into a somewhat hemispherical shell, forming the concave side of a filled blood chamber. Upon positive pressure through a drive line, the pumping membrane expanded and inverted itself to a convex hemispherical configuration, reducing the volume of the blood chamber and forcing the blood to exit through a valved outlet. During the course of its traverse from a retracted position in full hemispherical shape to the extended, convex configuration, the diaphragm passes through an intermediate, transitory condition wherein multiple uni- and biaxial folds occur within the diaphragm structure. A primary challenge of diaphragm design has been to minimize such folding and to reduce recurrence of common fold patterns which eventually weaken the affected area of the diaphragm. One area of focus in prior art techniques has involved design of a diaphragm which avoids predictable or repetitive fold pattern, and favors a random folding experience which protects the elastomer against localized stress.

In most cases, conventional design of the semi-rigid wall of the pumping chamber has retained a concave configuration to facilitate collapse of the diaphragm into a retracted position. See for example, U.S. Pat. Nos. 4,427,470 and 4,573,997 showing various prior art ventrical configurations having a separate rigid wall for each ventricle.

U.S. Pat. No. 4,750,903 represents a shift in diaphragm design for a TAH wherein a single, intermediate rigid septum or wall forms a base for each opposing ventricle. Furthermore, the direction of pumping movement for the diaphragm is lateral or somewhat parallel with respect to this wall, rather than normal thereto. According to this design, the pumping membrane is configured to collapse and extend to and from a vertical support which projects upward from the rigid base, resulting in diaphragm movement in a lateral orientation, as opposed to the conventional pattern of collapsing the diaphragm to or extending it away from the rigid wall.

Although this strategy of diaphragm design avoids adverse folding of the diaphragm, it introduces a new range of problems, including oriented drive lines which enter from a remote position with respect to the rigid base, in contrast with the more conventional approach of having the drive line establish pressure at the base and diaphragm juncture. This necessitates use of a central support column to maintain the drive line and diaphragm in a separated position from the rigid base.

Other problems will be apparent to those skilled in the art, including not only technical problems within the artificial heart structure, but thoracic space limitations relative to opposing drive line connections on opposite sides of the total artificial heart structure. When viewed in comparison with earlier prior art artificial ventricles, the trends in design generally appear to be raising unnecessary new problems, rather than solving old ones. What is needed is a simple artificial heart structure that enhances reliability and efficiency, while retaining structural simplicity.

OBJECTS AND SUMMARY OF THE INVENTION

It is an object of the present invention to provide a simple design strategy involving diaphragm structures which avoid overlapping uniaxial and biaxial folds and resultant localized stress, but which do not adversely minimize stroke volume of the ventricle.

A further object of the present invention is to provide a single heart septum and adjoining diaphragm configuration which reduces the angular extent of diaphragm movement when phasing between systole and diastole.

Yet another object of the present invention is to provide an improved design for a pumping diaphragm and rigid septum between the opposing ventricles of the total artificial heart which enable a reduced size and which more naturally conforms to a true heart shape.

A still further object of this invention is to provide an improved heart design which is capable of reduction to the small heart size of a neonate or infant.

Yet another object of this invention is to provide an enhanced drive line which more effectively delivers positive and negative pressure to the pumping chamber and reduces likelihood of infection at the percutaneous point of entry.

These and other objects are realized in a total artificial heart which comprises a heart enclosure approximately configured in the shape of a natural heart and which has a blood compatible interior surface. A rigid septum or base is attached at its periphery to the interior surface of the heart enclosure and operates to divide the enclosure into two separate pumping chambers, corresponding to left and right ventricles. These respective chambers are defined by the exposed faces of the septum which extend at a junction to include the respective interior surfaces of the heart enclosure in a continuous manner. The septum faces are designed with a non-planar configuration which includes a curved wave form to thereby increase the surface area of the septum to be almost equal to that surface area of the interior chamber surface to which the diaphragm extends during the pumping sequence. Each chamber includes a pumping diaphragm attached at a periphery near the juncture of the septum and heart enclosure to divide each chamber into (i) a pumping compartment formed between the face of the septum and adjacent diaphragm and (ii) a blood compartment formed by the diaphragm and the remaining interior surface of the heart enclosure. The diaphragm is geometrically configured with a wave form corresponding to the wave form of the septum face with sufficient common configuration to permit the diaphragm to nest without overlapping folds on the face of the septum and develop substantial maximum volume for the blood chamber when in a non-extended condition. Drive lines are coupled into the respective pumping chambers to enable the extension and retraction of the diaphragm in a conventional pumping sequence. Valved inlet and outlet means are coupled through the heart enclosure to each blood chamber to control inflow and outflow of blood from the respective ventricles. An improved drive line is also described, utilizing a double lumen tube split at one end to couple each respective pumping chamber.

Other objects and features of the present invention will be apparent to those skilled in the art based on the following detailed description, taken in combination with the accompanying drawings.

DETAILED DESCRIPTION OF THE INVENTION

Figure 1:
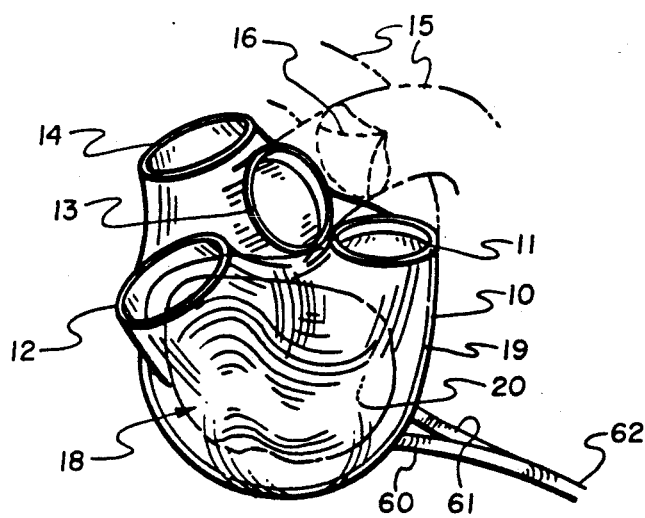
FIG. 1 shows a perspective view of a total artificial heart having the approved monoseptum, biventricular design in one embodiment of the present invention.

Referring now to the drawings:

FIG. 1 shows one embodiment of a total artificial heart as constructed in accordance with the present invention. It comprises a heart enclosure 10 which closely resembles the configuration and shape of a natural heart including heart openings 11, 12 and 13 and 14 which are aligned in a crossover pattern enabling suturing of inlet and outlet grafts or cuffs 15 having valve means 16 for controlling inflow and outflow with respect to interior chambers of the heart 10.

The left side (back side of FIG. 1) of the heart enclosure or housing provides atrial inflow through opening 14 and aortic outflow through opening 13, while the right side provides pulmonary outflow through opening 11 and atrial inflow through opening 12. All interior surfaces of the enclosure 10 are formed of materials which are blood compatible. Polyurethane material is appropriate for the housing, but many other accepted, blood compatible polymers are available. The selected polymer should have sufficiently high modulus of elasticity to resist collapse upon experiencing negative pressure from within the heart enclosure. Conventional mold casting techniques may be applied to prepare the subject enclosure 10.

A key element of this artificial heart is a rigid septum 18 which is attached at its periphery 19 to the interior surface of the heart enclosure and operates to divide the enclosure into the respective two ventricles or pumping chambers. Accordingly, these ventricles are respectively defined by an exposed face 20 of the septum and that portion of the interior surface of the heart enclosure which connects at a junction with the septum near its periphery 19 and extends in a continuous manner to enclose the chamber.

Figure 2:
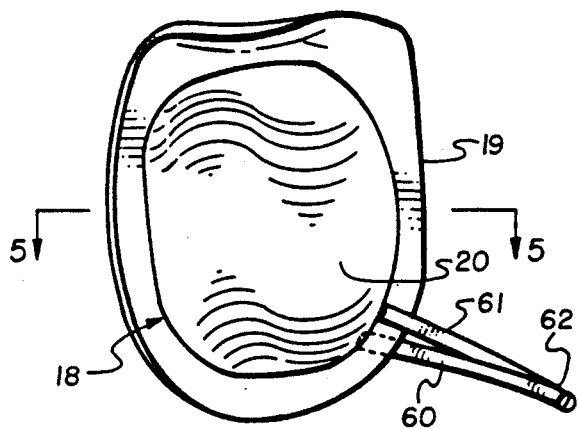
FIG. 2 shows a perspective view of the septum of FIG. 1, without the heart enclosure.
Figure 3:
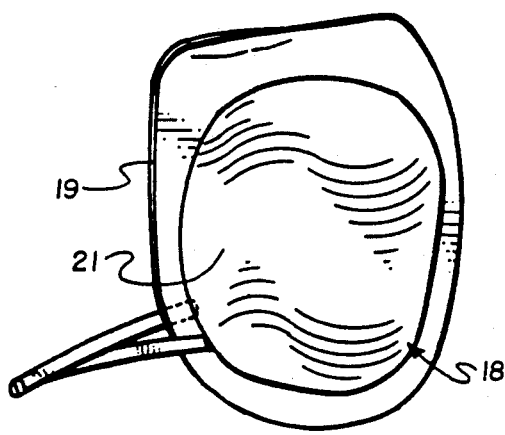
FIG. 3 shows an opposing view of the septum, taken from the back side of FIG. 2.

This septum is isolated in FIGS. 2 and 3, with front and back views being respectively provided. In FIG. 3, the exposed face 21 corresponds to exposed face 20 in FIG. 2. These respective faces provide a rigid surface against which pumping diaphragms 22 and 23 retract and extend to perform their blood pumping functions.

Figure 4:
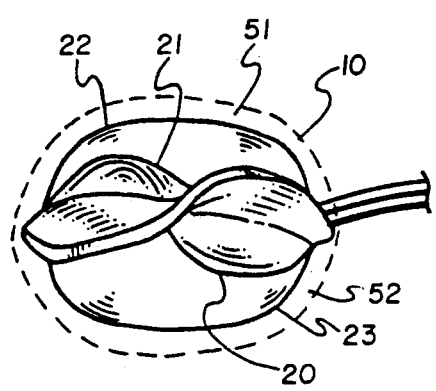
FIG. 4 shows a top view of the septum of FIG. 2, with opposing diaphragms inflated as at the end diastole.
Figure 5:
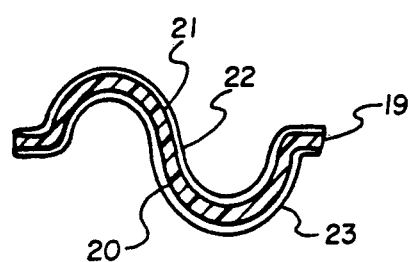
FIG. 5 shows a cross section of the septum of FIG. 2, taken along the lines 5—5.

It should be noted that these respective faces on the septum are non-planar in configuration and include a curved wave form along both verticle and horizontal axes with an "S" configuration at the horizontal axis as illustrated in FIG. 5. One purpose of this wave form is to greatly increase the surface area of faces 20 and 21 to be almost equal to the surface area of the interior surface of the heart enclosure within the chamber. In other words, the extended positions 22 and 23 of the pumping diaphragms as illustrated in FIG. 4, have surface areas which approximate more closely the surface area of the respective faces of the septum 20 and 21.

This is in contrast to prior art pumping chamber designs wherein the extended position of the diaphragm was an inverted, convex version of the retracted, concave form of the diaphragm at the end of diastole. The present invention to the contrary, shifts away from a mere concave form, to a wave form structure which includes some form of S configuration which develop increased surface area on each face of the septum.

Figure 9:
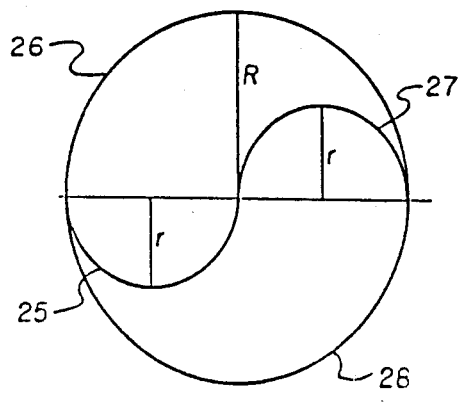
FIGS. 9 and 10 illustrate geometric patterns of certain design perimeters and lengths of "S" wave forms as compared to circular arcs.
Figure 10:
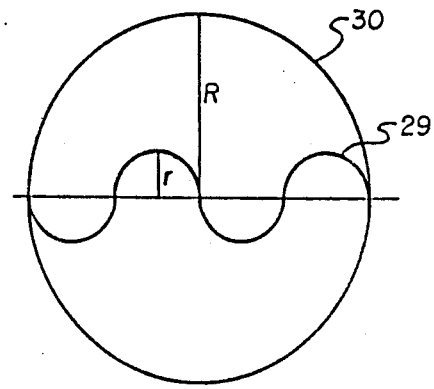

FIGS. 9 and 10 illustrate the principle of increased surface areas by virtue of comparisons of arc lengths of given radii. In FIG. 9, the radius represented by "r" is equal to one half the radius "R". The length of arc segment 25 equals r and the length of semi-circle arc section 26 similarly equals R. As much as R equals 2 r, it is evident that the combined length of arc lengths 25 and 27 equals the semicircular length of arc 26. Therefore, if arc segments 25 and 27 were viewed as a pumping diaphragm, it can be seen that its length will extend to the position at arc segment 26. Whereas common prior art techniques required the diaphragm retract to the concave arc position represented by lower segment 28, the present invention permits the diaphragm to retract only half the distance to a position of near equal surface area by adopting a wave form septum.

Similar comparisons between "r" and "R" can be made with respect to FIG. 10. In this instance R=4 r by virtue of the same rational applied in the preceding paragraph. In view of this disclosure, it will be apparent to those skilled in the art that the use of a wave form in single or multiple combinations may be applied to septum design to establish common surface areas between the retracted, wave configuration 29 and the extended semi-circular configuration 30. Similarly, one might compare the retracted configuration 25 and 27 with the geometry of item 21 in FIG. 4, and the extended configuration 26 to the geometry of the extended diaphragm 22. It will be noted hereafter that the illustrated wave forms represented by an "S" configuration or sinus wave are not the only available configurations which provide the appropriate increased surface area. Therefore, reference to "S" configuration is intended to broadly comprehend a variety of wave forms for a rigid septum which enable its use to divide the two ventricles of a total artificial heart, allowing both opposing diaphragms to expand to a full convex form from a configuration having both convex and significant concave elements. As used here, "significant" means capable of contributing to a significant increase in surface area on the septum face, rather than merely a nominal increase such as where the periphery of the rigid wall may have slight concave form to reduce blood stasis and clot formation which might otherwise occur around the periphery of the blood chamber.

Figure 6:
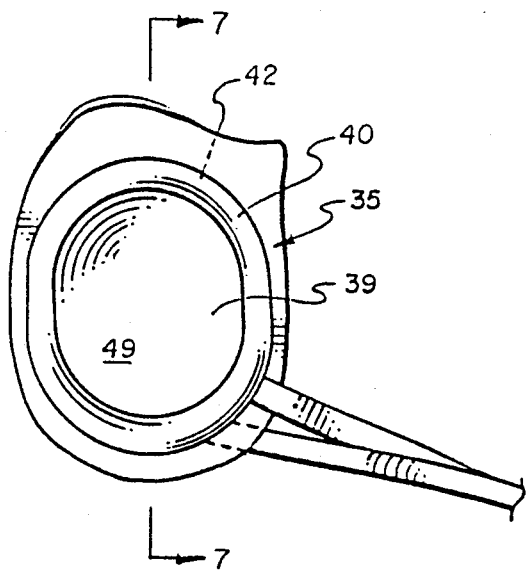
FIG. 6 shows a second embodiment of a septum incorporating a multiple "S" wave form of the present design.
Figure 7:
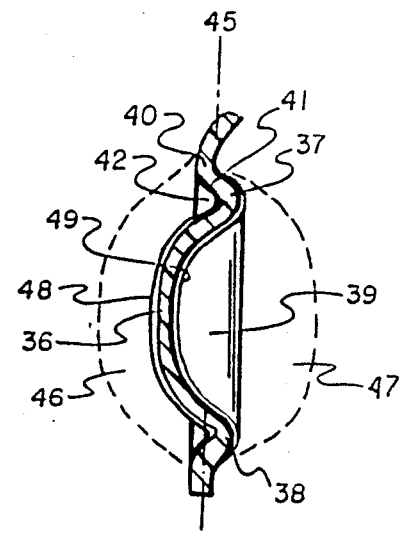
FIG. 7 is a cross section of the septum of FIG. 6, taken along the lines 7—7, with an associated geometric pattern.
Figure 8:
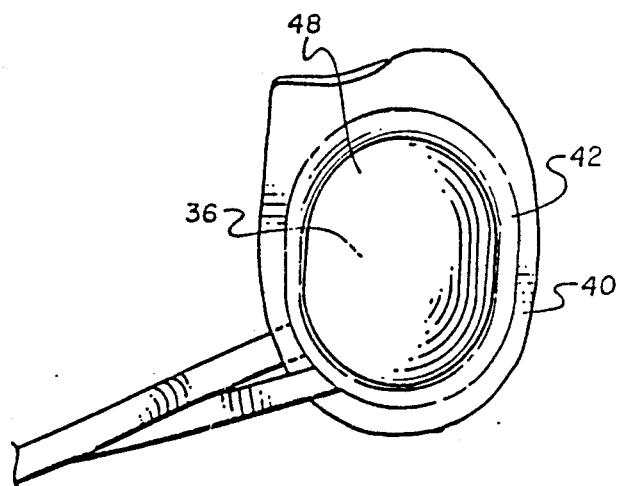
FIG. 8 is a view of the septum of FIG. 6, as seen from the back side of the drawing.

FIGS. 6, 7 and 8 illustrate a second embodiment wherein the septum 35 includes the curved wave form configured at its cross section in the form of a "U" 36 with smaller and inverted "u" shapes 37 and 38 integrally formed with terminal end portions of each leg of the "U" 36. This has been graphically illustrated in FIG. 7 in side-by-side relationship to facilitate visualization of this configuration. From a different perspective, this additional embodiment can be viewed as a dome having a concave or open side 39 and further including a peripheral lip 40 which is continuous with and extends around the perimeter of the dome to form a continuous channel 41 having an inverted, opposing channel opening 42 as compared with the open side 39 of the dome.

This second embodiment represents a non-symmetrical configuration as viewed about a central plane 45 of the elongate axis for the septum. This is in contrast to the somewhat symmetrical form illustrated in FIGS. 2 through 5 wherein the wave form is a symmetrical "S" configuration. A performance consideration of the non-symmetrical embodiment of FIGS. 6 through 8 includes a pumping difference wherein one pumping chamber 46 has a lesser pumping capacity than its opposing pumping chamber 47. In this case, these chambers would be designated as right and left ventricles respectively. As with the earlier described embodiment, the dome shaped embodiment of FIGS. 6, 7 and 8 also includes a pumping diaphragm at each side of the dome 48 and 49 which extends to the respective positions identified at items 46 and 47.

The construction of the septum needs to be rigid to provide resilience against the positive and, if needed, negative pressures which operate the respective diaphragms. If the septum were able to deform, the attached membrane would be stressed and vulnerable to failure. Such deformation would also modify the stroke volume to a lesser capacity. In its preferred form, the septum should be thin, as well as rigid, and should include a curve on the boundaries where the septum joins with the pumping diaphragm and heart enclosure. This is in accordance with accepted practice of minimizing dead space within the blood pumping chamber, to thereby reduce likelihood of blood clot formation. Additional conventional design features will not be discussed herein to the extent that those skilled in the art would understand the importance of bringing forward enhancements from prior art heart design to the present improved septum design as disclosed herein.

Figure 11:
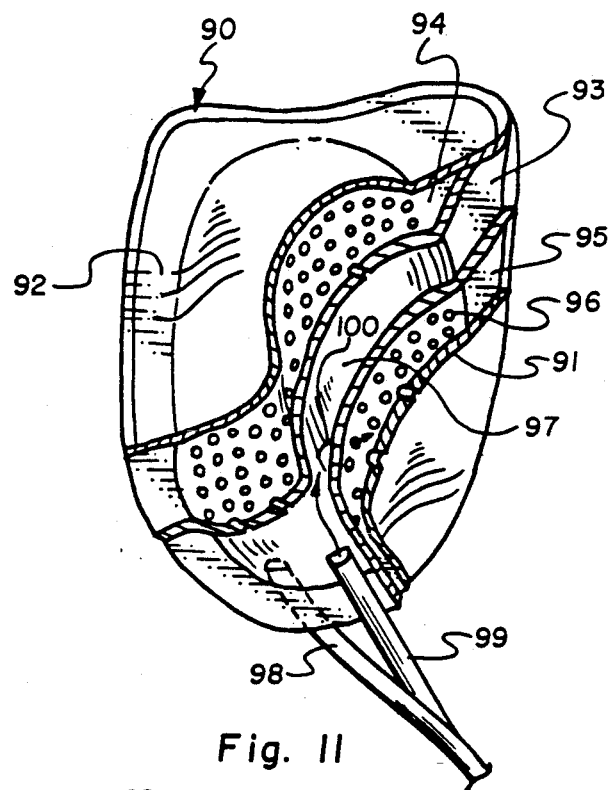
FIG. 11 shows a cut-away, sectional view of a septum and pumping diaphragm combination in accordance with an additional embodiment of the present invention.

One material suitable for developing the needed rigidity of the present septum is ISOPLAST 301 (trademark of Dow Chemical). This material can be machined to any of the proposed configurations. The septum may be formed as a single, rigid structure or may be formed in multiple wall segments as is illustrated in FIG. 11, which will be discussed in greater detail hereafter.

Returning to the description of the heart construction, each chamber includes a pumping diaphragm which resembles a skin overlay 22 and 23 on the respective faces 20 and 21. The pumping diaphragm functions to divide each chamber into (i) a pumping compartment between the face 20, 21 of the septum and the adjacent diaphragm 22 and 23, and (ii) a blood compartment 51, 52 formed by the diaphragm structure 22, 23 and the remaining interior surface of the heart enclosure 10 as shown in FIG. 4.

The diaphragm 22, 23 is geometrically configured with a wave form corresponding to the wave form of the septum sufficient to permit the diaphragm to nest thereon without an overlapping fold on the face of the septum 20, 21 and to develop maximum volume for the blood chamber when in nonextended condition (FIG. 5). This is accomplished by forming the diaphragm on a mold or mandrel of comparable configuration to the respective faces of the septum 20 and 21. In this manner, the diaphragm polymer is biased to the wave form developed from its forming mandrel. Therefore, in the absence of exterior forces or with nominal negative pressure, the polymer is biased to assume its naturally molded wave configuration as illustrated in FIG. 5. Upon imposition of positive pressure within the pumping chamber, respective diaphragms 22 and 23 extend to the configuration shown in FIG. 4. This configuration, however, is not the natural configuration of the diaphragm polymer. Upon release of this positive pressure, or with slight suction, the polymer naturally returns to its wave form configuration as is illustrated in FIG. 5.

This diaphragm or pumping membrane can be formed as a continuous membrane by solution casting techniques on the inside of the housing over molds shaped like the actual septum. This selected material may naturally bond with the housing interior surface and may include such polymers as Biomer (TM) and polyurethane or other blood compatible materials. Graphite lubrication and other conventional techniques to protect the diaphragm and properly configure and engineer its emplacement should also be applied and are well known within the art.

Figure 12:
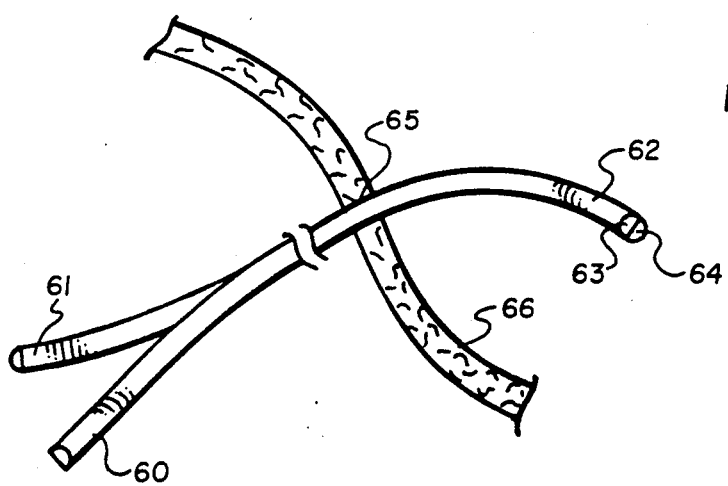
FIG. 12 shows a double lumen drive line in percutaneous configuration.

The pumping membranes are powered by a pneumatical drive system through drive lines 60 and 61. These drive lines are coupled to the respective pumping compartments to enable delivery of positive and negative air pressure to extend and retract the diaphragm in accordance with conventional methods. A unique feature of the present design is utilization of a double lumen tube 62 which is more particularly shown in FIG. 12. This tube has two separate lumen or flow lines 63 and 64. These flow lines separate into the respective tube ends 60 and 61, which are attached into the pumping compartments. Each tube end has a "D" configuration with a flat side 69 which can be positioned directly against the face of the septum. The split ends automatically facilitate positioning of flat sections on each septum.

Figure 13:
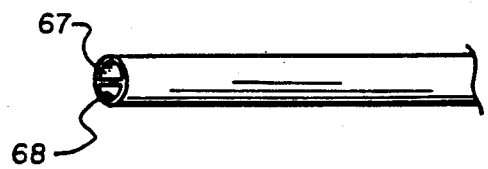
FIG. 13 illustrates an additional configuration for a double lumen tube with elliptical cross section.

Another advantage of the double lumen tube is reduction in the number of openings 65 through the skin 66. This reduces the likelihood of infection and related complications. FIG. 13 shows an elliptical cross section wherein the respective lumen 67 and 68 are cross sections of the elliptical opening. This tube likewise would split at 10 to form two separate tubes for attachment to the pumping compartments.

It will be apparent to those skilled in the art that this percutaneous device will be useful for other fluid delivery circumstances in addition to pneumatic applications. This distinctive characteristic includes a single tube having a double lumen for providing two separate fluid paths respectively. Typically this tube will have at least one of its ends with two separate ends split out from the single, double lumen tube and communicating in line with openings of the double lumen. Such terminally separated tubes will typically include means for attaching or coupling to pumping chambers or whatever structure is appropriate to accomplish the attended purpose.

Finally, the total artificial heart includes drive inlet and outlet means as previously mentioned. The particular value of the present invention with its monoseptum and curved configuration is the ability to reduce the size of a heart to a form suitable for implantation within new born infants. Because of the improved crossover configuration facilitated by the monoseptum and its wave form, the heart may be reduced to such a small size that even a new born neonate with its extreme limited thoracic space may be the beneficiary of a total artificial heart pending availability of a transplant. It is believed that between 2,000 and 3,000 infants and small children a year are in need of such a life support system which has heretofore been unavailable. The present heart design now permits applications of total artificial heart technology to children, infants and neonates.

It will be apparent to those skilled in the art that numerous variations may be developed which incorporate the inventive principles disclosed herein. For example, this structure could be used in an extracorporeal application as a monoseptal bi-ventricular assist device. Also, multiple diaphragms can be used in accordance with customary practice of having separate blood contacting membrane in combination with a pumping diaphragm. An additional variation is illustrated in FIG. 11, showing a septum design where the pressurized drive fluid feeds through a perforated septum wall, in contrast to direct entry and exit into the pumping chamber. Specifically, FIG. 11 illustrates a rigid septum 90 with an attached pumping diaphragm or skin 91, 92 coupled in accordance with previous disclosure. This septum has an "S" curve configuration to incorporate the required increased surface area on the face of the septum. This septum itself is comprised of an interior rigid wall 93 which operates as the base for both faces or both sides of the septum structure. Each side then has an adjacent perforated wall 94 and 95 including numerous small openings 96 which permit fluid flow from a fluid delivery chamber 97. This fluid flows in from the respective drive lines 98 and 99 and through the perforated wall 96 as illustrated by arrow 100. The perforated walls 94 and 95 spread the fluid pressure across the entire surface of the diaphragm 91, 92 rather than loading the diaphragm near the entrance of fluid from tube 99 and causing stress in this local area.

Other variations will be conceivable by those skilled in the art. Accordingly, the foregoing description is given by way of example and not for the purpose of limiting the appended claims to this disclosure.

I claim:

1. An artificial heart or biventricular assist device, comprising:

a heart enclosure approximately configured in the shape of a natural heart and having a blood compatible interior surface;

a rigid septum attached at its periphery to the interior surface of the heart enclosure and operable to divide the enclosure into two separate pumping chambers corresponding to left and right ventricles, said chambers being respectively defined by an exposed face on each side of the septum and that portion of the interior surface of the heart enclosure which connects at a junction with the septum and extends in a continuous manner to enclose the respective chambers;

said exposed faces of the septum having vertical and horizontal axes and a nonplanar configuration along said axes including a curved wave form with an "S" configuration to increase surface area of each septum face to be almost equal to the surface area of the interior surface of the heart enclosure within the corresponding chamber;

each chamber including a pumping diaphragm attached at its periphery near the juncture of the septum and heart enclosure to divide each chamber into (i) a pumping compartment formed between the face of the septum and the adjacent diaphragm, and (ii) a blood compartment formed by the diaphragm and the remaining interior surface of the heart enclosure;

said diaphragm being geometrically configured with a wave form corresponding to the wave form of the corresponding septum face sufficient to permit the diaphragm to nest without an overlapping fold on the face of the septum and develop substantial maximum volume for the blood chamber when in nonextended condition, yet to extend to a domed configuration within the respective compartments and force blood from the blood chamber;

first and second drive lines coupled to the respective pumping compartments to enable delivery of fluid pressure to extend and retract the diaphragm to thereby operate the pumping chambers; and valved inlet and outlet means coupled through the heart enclosure to each blood chamber to control inflow and outflow of blood.

2. An artificial heart as defined in claim 1, wherein the respective valved inlet and outlet means are configured in a cross-over relationship comparable to the atria, aorta and pulmonary artery openings of a natural heart, an upper section and periphery of the septum being contoured away from a central plane of the septum to provide a unobstructed flow line between the blood chamber of each ventricle and the connecting crossover inlet and outlet means.

3. An artificial heart as defined in claim 2, wherein the heart is dimensioned in size and pumping capacity to fit within and service a neonate, infant or child.

4. An artificial heart as defined in claim 1, wherein the curved form of each septum face is configured in a single "S" form.

5. An artificial heart as defined in claim 1, wherein the curved wave form of each septum face is configured in the form of a sinus wave.

6. An artificial heart as defined in claim 1, wherein the curved wave form of each septum face is configured along each axis in the form of a large "U" with smaller inverted "u" shapes integrally formed with terminal end portions of each leg of the large "U".

7. An artificial heart as defined in claim 1, wherein the wave form is symmetrical about a central plane of its axes.

8. An artificial heart as defined in claim 1, wherein the wave form is nonsymmetrical about a central plane of its axes, one pumping chamber having lesser pumping capacity, and being designated as the right ventricle, than the remaining chamber being designated as the left ventricle.

9. An artificial heart as defined in claim 1, wherein the exposed faces of the septum are formed in the shape of a dome having a concave, open side and further including a peripheral lip continuous with and extending around the perimeter of the dome to form a continuous channel having an inverted, opposing channel opening as compared with the open side of the dome.

10. An artificial heart as defined in claim 1, wherein the drive line comprises a single tube having a double lumen for providing positive and negative fluid pressure respectively, the tube having at least one end with two separate tubes split off from the single tube and communicating in line with openings of the double lumen, said separate tubes being coupled to the respective pumping chambers of the artificial heart.

11. An artificial heart as defined in claim 10, wherein the double lumen tube includes separate tubes which respectively have a "D" cross-section with a flat side of the "D" for each tube being contiguous, said flat sides being coupled directly at the opposing faces of the septum and the rounded side providing open fluid flow into the pumping chamber.

* * * * *

UNITED STATES PATENT AND TRADEMARK OFFICE
CERTIFICATE OF CORRECTION

PATENT NO. : 5,089,020
DATED : February 18, 1992
INVENTOR(S) : Erik Koppert

It is certified that error appears in the above-identified patent and that said Letters Patent is hereby corrected as shown below:

Column 1, line 4:
Insert after Title of Invention and preceding Background of the Invention:

"This invention was made with government support under Grant Number NIH 5-R01-HL-38304-02 awarded by the Department of Health & Human Services/Institute of Health. The government has certain rights in the invention".

Signed and Sealed this

Twenty-fifth Day of May, 1993

Attest:

MICHAEL K. KIRK

Attesting Officer

Acting Commissioner of Patents and Trademarks